(12) United States Patent
Torp et al.

(10) Patent No.: US 7,678,052 B2
(45) Date of Patent: Mar. 16, 2010

(54) METHOD AND APPARATUS FOR DETECTING ANATOMIC STRUCTURES

(75) Inventors: Anders Herman Torp, Oslo (NO); Stein Inge Rabben, Sofiemyr (NO); Bjørn Olstad, Stathelle (NO)

(73) Assignee: General Electric Company, Schenectady, NY (US)

( * ) Notice: Subject to any disclaimer, the term of this patent is extended or adjusted under 35 U.S.C. 154(b) by 1510 days.

(21) Appl. No.: 10/822,935

(22) Filed: Apr. 13, 2004

(65) Prior Publication Data

US 2005/0228254 A1    Oct. 13, 2005

(51) Int. Cl.
*A61B 8/00* (2006.01)
*A61B 5/05* (2006.01)
*G06F 9/00* (2006.01)

(52) U.S. Cl. .................. 600/450; 600/451; 600/407; 382/128

(58) Field of Classification Search ................ 600/450, 600/443–437; 382/128, 131, 173; 345/419
See application file for complete search history.

(56) References Cited

U.S. PATENT DOCUMENTS

| 6,106,465 | A | 8/2000 | Napolitano et al. |
| 6,106,466 | A * | 8/2000 | Sheehan et al. ............ 600/443 |
| 2002/0072671 | A1* | 6/2002 | Chenal et al. ............... 600/450 |
| 2003/0160786 | A1* | 8/2003 | Johnson .................... 345/419 |
| 2004/0037455 | A1* | 2/2004 | Klingensmith et al. ...... 382/128 |

* cited by examiner

*Primary Examiner*—Eric F Winakur
*Assistant Examiner*—Lawrence N Laryea
(74) *Attorney, Agent, or Firm*—Dean D. Small; Small Patent Law Group

(57) ABSTRACT

An anatomic structure is detected based on a medical diagnostic imaging data set. The anatomic structure comprises at least two different types of tissue. At least one anatomic landmark is identified within the data set, the data set is overlaid with a contour template, and a search region of the data set surrounding the contour template is scanned to identify transition points associated with a predefined characteristic of the anatomic structure.

21 Claims, 8 Drawing Sheets

Prior to Temporal Smoothing

| Image Frame 1 | Image Frame 2 | Image Frame 3 | Image Frame N |
|---|---|---|---|
| $D_{1A}$ | $D_{1A}$ | $D_{1A}$ | $D_{1A}$ |
| $D_{2A}$ | $D_{2A}$ | $D_{2A}$ | $D_{2A}$ |
| $D_{3A}$ | $D_{3A}$ | $D_{3A}$ | $D_{3A}$ |
| $D_{4A}$ | $D_{4A}$ | $D_{4A}$ | $D_{4A}$ |
| $D_{5A}$ | $D_{5A}$ | $D_{5A}$ | $D_{5A}$ |
| $D_{6A}$ | $D_{6A}$ | $D_{6A}$ | $D_{6A}$ |
| $D_{NA}$ | $D_{NA}$ | $D_{NA}$ | $D_{NA}$ |

FIG. 9

After Temporal Smoothing

| Image Frame 1 | Image Frame 2 | Image Frame 3 | Image Frame N |
|---|---|---|---|
| $D_{1AVE}$ | $D_{1AVE}$ | $D_{1AVE}$ | $D_{1AVE}$ |
| $D_{2AVE}$ | $D_{2AVE}$ | $D_{2AVE}$ | $D_{2AVE}$ |
| $D_{3AVE}$ | $D_{3AVE}$ | $D_{3AVE}$ | $D_{3AVE}$ |
| $D_{4AVE}$ | $D_{4AVE}$ | $D_{4AVE}$ | $D_{4AVE}$ |
| $D_{5AVE}$ | $D_{5AVE}$ | $D_{5AVE}$ | $D_{5AVE}$ |
| $D_{6AVE}$ | $D_{6AVE}$ | $D_{6AVE}$ | $D_{6AVE}$ |
| $D_{NAVE}$ | $D_{NAVE}$ | $D_{NAVE}$ | $D_{NAVE}$ |

FIG. 10

METHOD AND APPARATUS FOR DETECTING ANATOMIC STRUCTURES

BACKGROUND OF THE INVENTION

This invention relates generally to medical diagnostic systems. In particular, the present invention relates to methods and apparatus for acquiring and processing diagnostic data sets to identify the location of the transition between different types of tissue and between tissue and blood.

The processing of cardiac image data is of great interest to determine how the heart is functioning. Currently, many processing algorithms rely on the user to identify the data to be processed. In ultrasound, due to patient and system limitations, the user is often unable to precisely identify the location desired, such as the endocardium or epicardium. For example, the systems do not have the capability to allow the user to input precise measurements to track the minute variable contours of the tissue. In addition, the user has limited time with which to conduct the measurements.

For example, an important measurement for left ventricular function is the ejection fraction (EF), defined as the end-diastole (ED) volume minus the end-systolic (ES) volume of the left ventricle divided by ED volume. Today, this measurement is often estimated by manually drawing the endocardium at ED and ES in one or two planes. This is time consuming and the model assumes that the ventricle is symmetric along the diameter. Also, due to poor image quality in many patients, locating the volume automatically can be difficult.

Other imaging modalities also acquire cardiac images and experience the same problems. In addition, other anatomy or masses of interest, such as the liver, arteries, cysts and tumors, would benefit from the ability to more precisely identify the interface between two types of tissue.

Thus, a system and method are desired to process diagnostic data sets to identify the location of transitions within a body, that addresses the problems noted above and others previously experienced.

BRIEF DESCRIPTION OF THE INVENTION

A method is provided for detecting an anatomic structure based on a medical diagnostic imaging data set comprising obtaining a data set representative of a diagnostic image corresponding to an anatomic structure, identifying at least one anatomic landmark within the data set, overlaying the data set with a contour template, and scanning a search region of the data set surrounding the contour template to identify transition points associated with a predefined characteristic of the anatomic structure.

A system is provided for identifying an endocardium comprising a transmitter transmitting ultrasound signals into an area of interest, a receiver receiving echo signals from the transmitted ultrasound signals, and a memory storing a series of image frames comprising the echo signals. The series of image frames comprise at least one heart cycle. The system also comprises a signal processor processing the series of image frames to identify at least one of an apex and an AV plane having first and second ends, overlaying a contour template connecting the apex to the first and second ends on the series of image frames, and identifying and comparing points along the contour template to identify transition points based upon a predefined characteristic of an endocardium. The system also comprises an output for outputting information based on an output of the signal processor.

A method is provided for identifying a contour between different types of tissue comprising obtaining a series of data sets representative of a diagnostic image having at least two different types of tissue, identifying at least two anatomic landmarks within the series of data sets, and connecting at least two anatomic landmarks with a contour template. The method also comprises identifying data points on and around the contour template, and comparing the data points to identify transition points having a predefined characteristic indicative of a change from one type to a second type of tissue.

BRIEF DESCRIPTION OF THE DRAWINGS

FIG. 9 is a table with distance measurements representing contours of image frames prior to temporal smoothing in accordance with an embodiment of the present invention.

FIG. 10 is a table with distance measurements representing contours of image frames after temporal smoothing in accordance with an embodiment of the present invention.

DETAILED DESCRIPTION OF THE INVENTION

Figure 1:
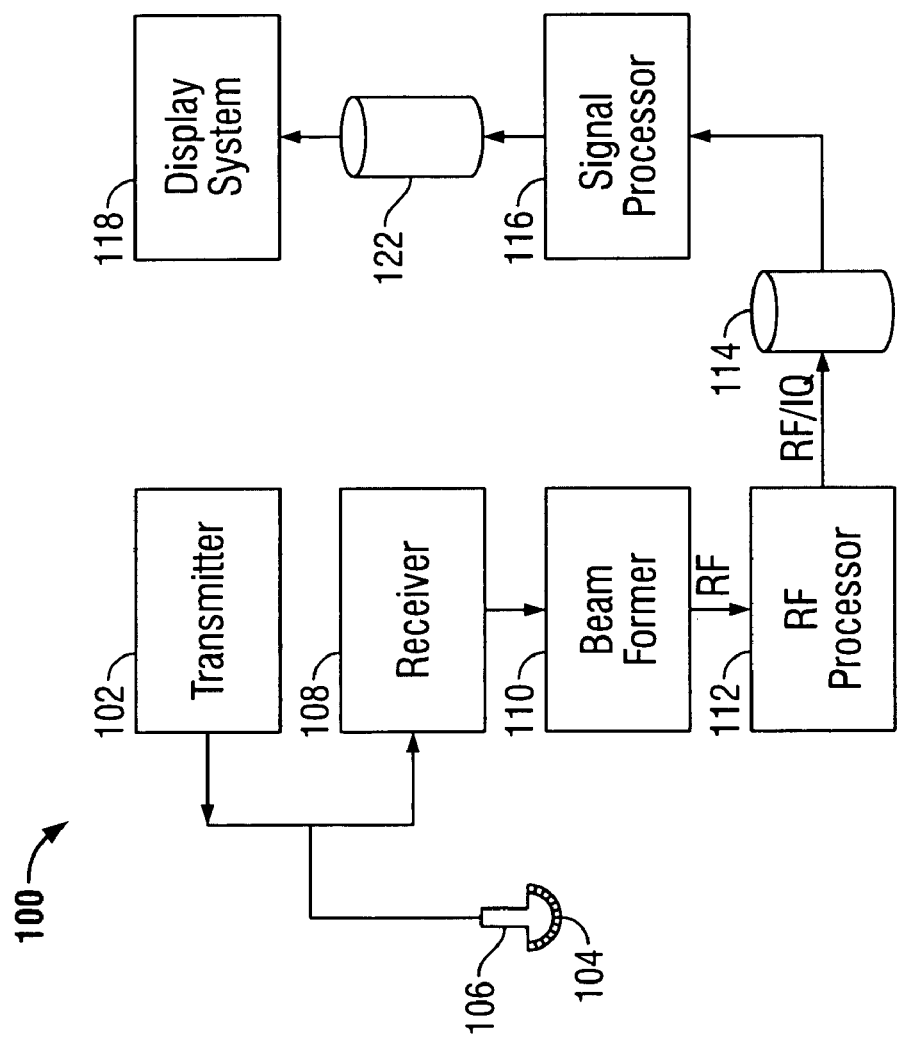
FIG. 1 illustrates a block diagram of an ultrasound system formed in accordance with an embodiment of the present invention.

FIG. 1 illustrates a block diagram of an ultrasound system 100 formed in accordance with an embodiment of the present invention. The ultrasound system 100 includes a transmitter 102 which drives an array of elements 104 within a transducer 106 to emit pulsed ultrasonic signals into a body. A variety of geometries may be used. The ultrasonic signals are backscattered from structures in the body, like blood cells or muscular tissue, to produce echoes which return to the elements 104. The echoes are received by a receiver 108. The received echoes are passed through a beamformer 110, which performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to RF/IQ buffer 114 for temporary storage.

The ultrasound system 100 also includes a signal processor 116 to process the acquired ultrasound information (i.e., RF signal data or IQ data pairs) and prepare frames of ultrasound information for display on display system 118. The signal processor 116 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in RF/IQ buffer 114 during a scanning session and processed in less than real-time in a live or off-line operation.

The ultrasound system 100 may continuously acquire ultrasound information at a frame rate that exceeds 50 frames per second—the approximate perception rate of the human eye. The acquired ultrasound information may be displayed on the display system 118 at a slower frame-rate. An image buffer 122 is included for storing processed frames of acquired ultrasound information that are not scheduled to be displayed immediately. Preferably, the image buffer 122 is of sufficient capacity to store at least several seconds worth of frames of ultrasound information. The frames of ultrasound information are stored in a manner to facilitate retrieval thereof according to its order or time of acquisition. The image buffer 122 may comprise any known data storage medium.

Figure 2:
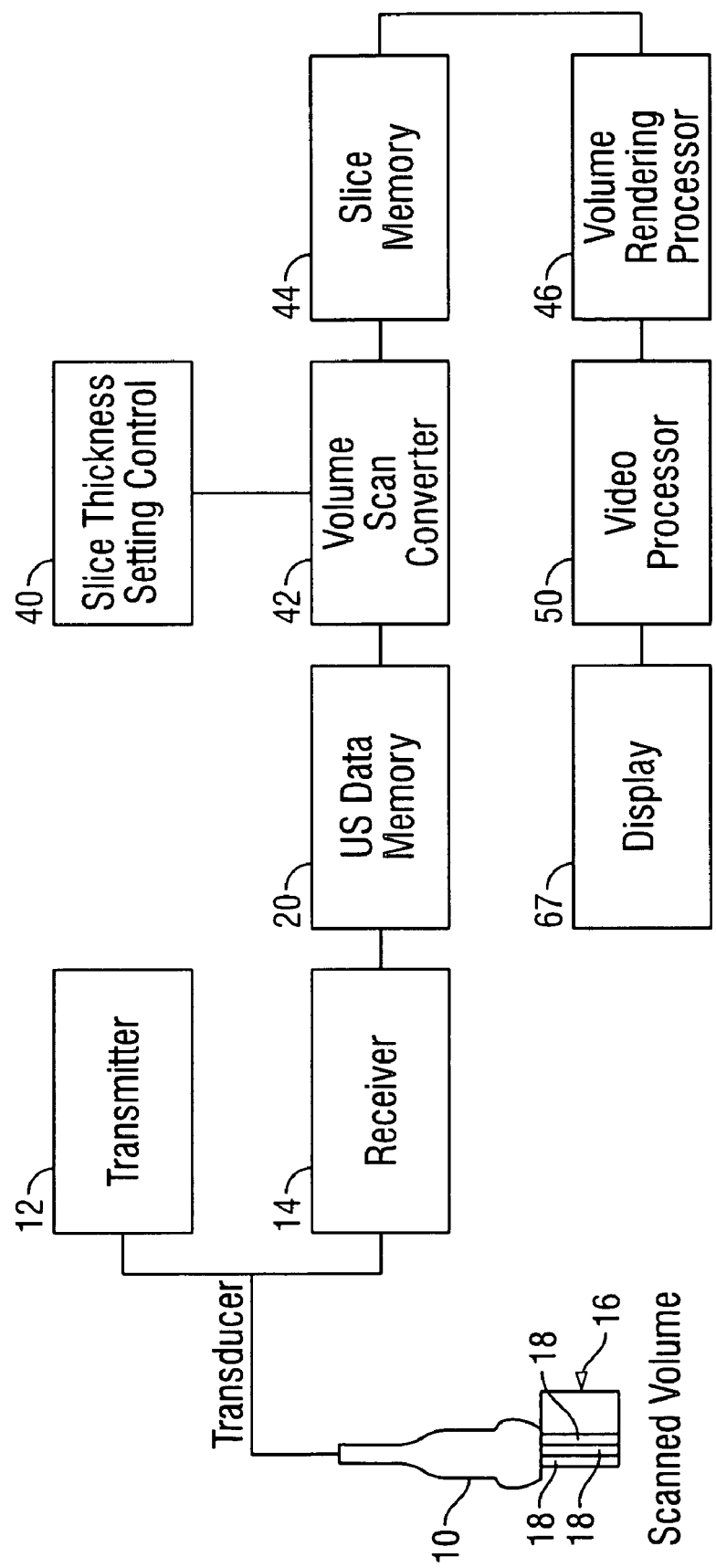
FIG. 2 illustrates an ultrasound system formed in accordance with an embodiment of the present invention.

FIG. 2 illustrates an ultrasound system formed in accordance with one embodiment of the present invention. The system includes a transducer 10 connected to a transmitter 12 and a receiver 14. The transducer 10 transmits ultrasonic pulses and receives echoes from structures inside of a scanned ultrasound image or volume 16. Memory 20 stores ultrasound data from the receiver 14 derived from the scanned ultrasound image or volume 16. The image or volume 16 may be obtained by various techniques (e.g., 3D scanning, real-time 3D imaging, volume scanning, 2D scanning with transducers having positioning sensors, freehand scanning using a Voxel correlation technique, 2D or matrix array transducers and the like).

The transducer 10 may be moved, such as along a linear or arcuate path, while scanning a region of interest (ROI). The scan planes 18 are stored in the memory 20, and then passed to a scan converter 42. In some embodiments, the transducer 10 may obtain lines instead of the scan planes 18, and the memory 20 may store lines obtained by the transducer 10 rather than the scan planes 18. The scan converter 42 may store lines obtained by the transducer 10 rather than the scan planes 18. The scan converter 42 creates a data slice from a single scan plane 18. The data slice is stored in slice memory 44 and then passed to the video processor 50 and display 67.

Figure 3:
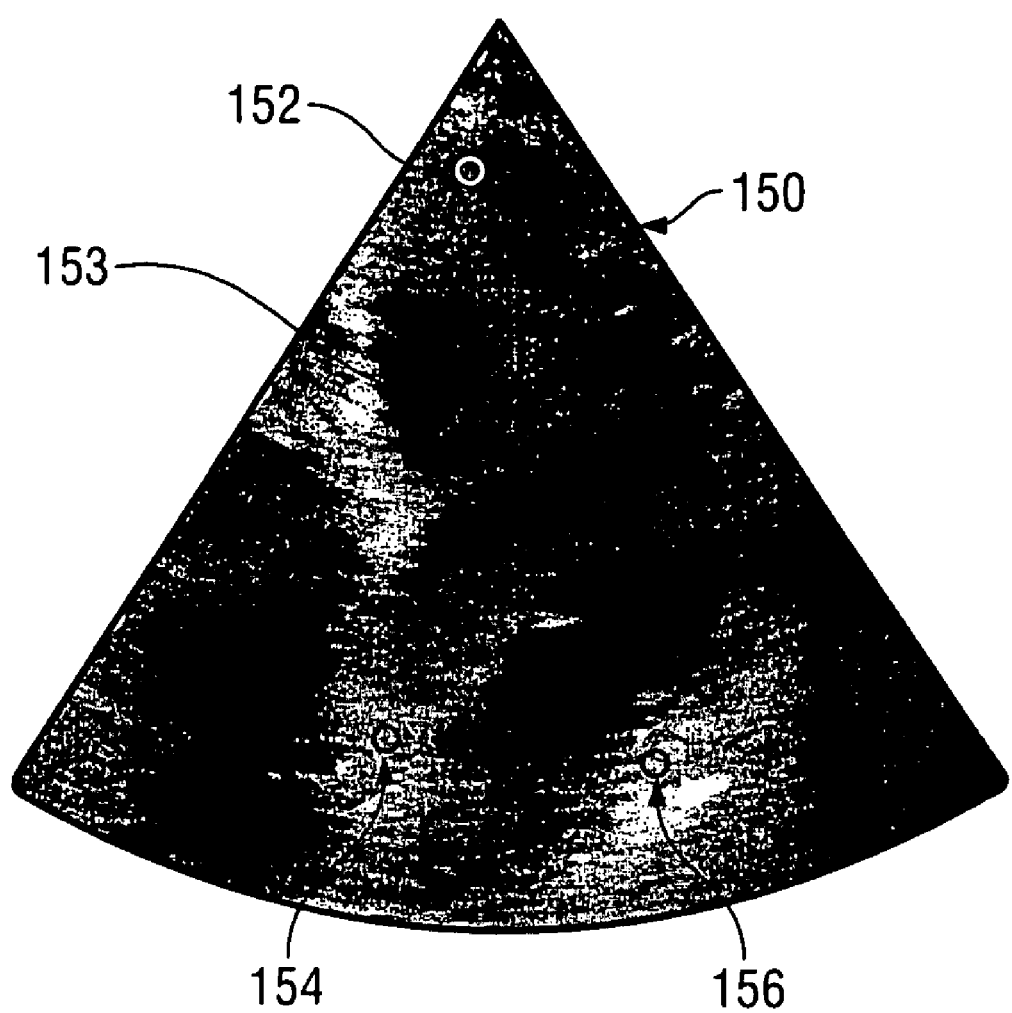
FIG. 3 illustrates an image frame with three anatomic landmarks indicated within a myocardium formed in accordance with an embodiment of the present invention.

FIG. 3 illustrates an image frame 150 with three anatomic landmarks indicated within a myocardium. The image frame 150 contains ultrasound data, although it should be understood that other imaging modalities may be used, such as CT, PET, SPECT, gamma camera, X-ray, and MR. For simplicity, the following discussion is limited to ultrasound, although the techniques discussed apply to other modalities. The image frame 150 also includes at least two different types of tissue, such as heart tissue and blood. When imaging other anatomy, the image frame 150 may include tissue of different density. In addition, contrast agent may be used to better differentiate edges.

A method using tissue velocity imaging (TVI) to locate the anatomical landmarks is discussed below, although other algorithms and methods may be used, such as speckle tracking. The signal processor 116 identifies a number of data points in the image, such as several hundred points (not shown). The points are identified with respect to the expected location of anatomic landmarks. By way of example only, in an apical view of the adult heart, the apex is commonly located approximately 2 cm from the transducer 106, and the AV plane is commonly located at approximately 10 cm from the transducer 106. Therefore, physically common ranges identified with respect to the expected locations of the landmarks may be identified as areas in which to identify the data points. The TVI information for each image frame 150 is analyzed to track each data point in time to determine movement and displacement. The data points are tracked during at least one heart cycle. The signal processor 116 may display and track the identified anatomical landmarks in live mode. Alternatively, at least one heart cycle may be acquired and then processed.

One anatomic landmark is the apex 152. The apex 152 is located at the top of the ventricle 153 in apical views. The apex is close to the transducer 106 in apical views and is almost motionless during a heart cycle. Only tissue should be above the apex 152 (i.e. no blood flow between the apex 152 and the transducer 106). The signal processor 116 scans line by line downward through the image frame 150 to locate high TVI values or movement of the data points to identify where blood is flowing. Also, the difference in brightness between data points may be compared to find a transition from bright to dark to identify the change from heart tissue to blood.

The other two anatomic landmarks indicate first and second ends 154 and 156 of the atrio-ventricular (AV) plane. The AV plane, or mitral ring, is the plane defined by the mitral valves located at the first and second ends 154 and 156. In apical views the AV plane is located in a generally horizontal plane of the image frame 150, or at 90 degrees with respect to the ultrasound beam. Also, the mitral ring is circular and has a diameter within a known range. In addition, the AV plane typically has more displacement than other segments of the ventricle within the image frame 150. Thus, maximum displacement of data points spatially towards and away from the transducer 106 is considered. To verify that the identified AV plane is within tissue and not blood, data points may be tracked in time. The data points within tissue will be located at the same position at both the start and end image frames 150 of the heart cycle. Blood flows in one direction at high velocity, and TVI is unable to calculate, due in part to aliasing effects. In addition, data points defined within blood will be located at completely different locations on the start and end image frames 150.

Figure 4:
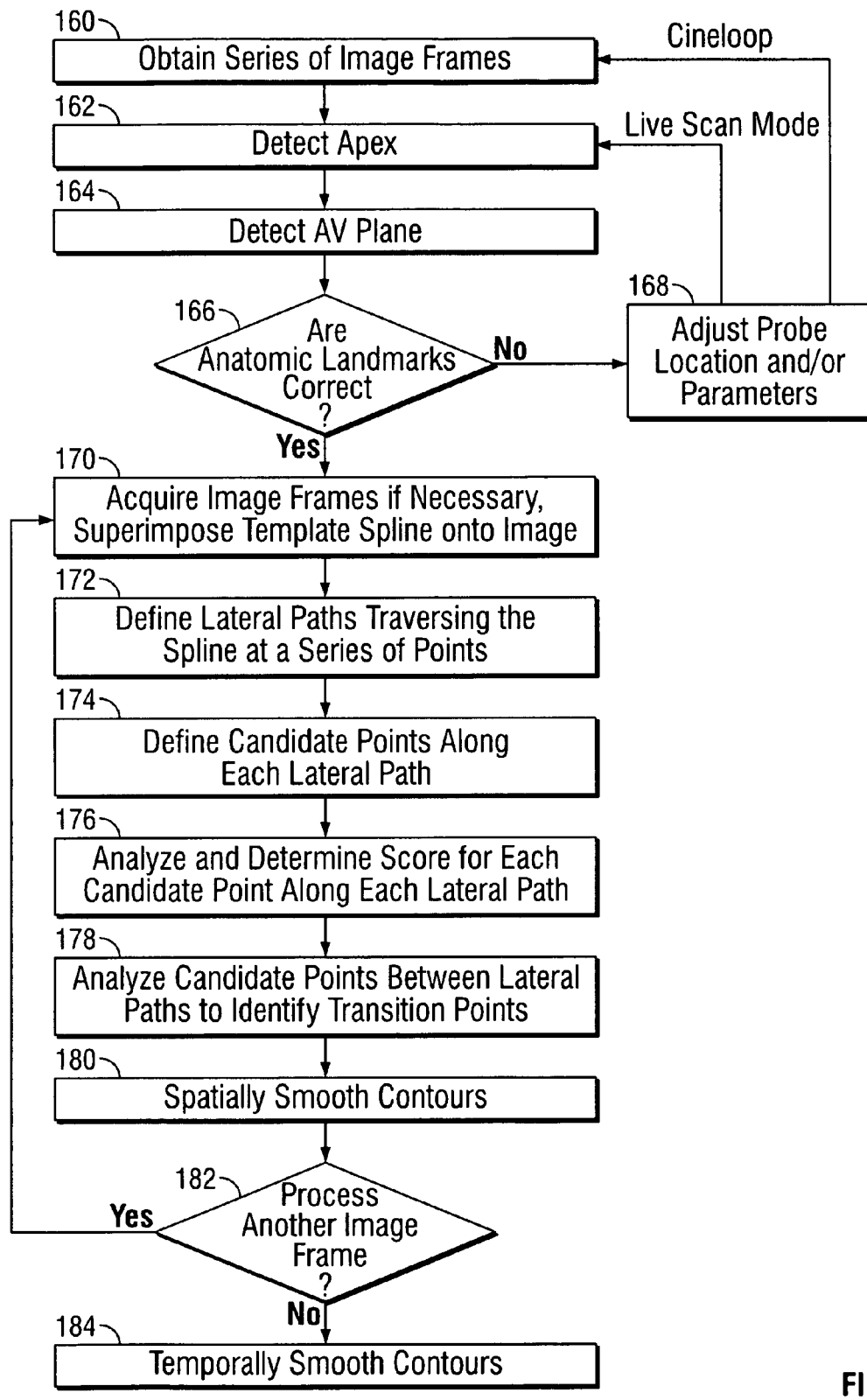
FIG. 4 illustrates a method for estimating the location of the endocardium in accordance with an embodiment of the present invention.

FIG. 4 illustrates a method for estimating the location of the endocardium by using edge detection. With the following method, a more accurately identified location of the endocardium is achieved, resulting in more accurate ejection fraction (EF) and other measurements. In step 160, a series of image frames 150 is acquired. The series of image frames 150 includes at least one heart cycle. The image frames 150 may be stored as a cineloop or processed live, for example. The image frames 150 may also be stored as data sets in the RF/IQ buffer 114 (FIG. 1) or memory 20 (FIG. 2). By way of example only, the image frames 150 may comprise 2D or TVI modes as discussed previously. It should be understood that the acquisition is not limited to the modes listed here.

In steps 162 and 164, the signal processor 116 automatically detects the apex 152 and AV plane as discussed previously. At this point, the user reviews the apical 4 chamber view, or other acquired view, to verify that the anatomic landmarks (apex 152 and ends 154 and 156 of the AV plane) are correctly located (step 166). If the anatomic landmarks are not correct, flow passes to step 168. In step 168, the user may move the transducer 106 or use a user input to select other scanning parameters until the correct apex and AV plane are located. If stored data sets are being used, flow passes to step 170. Alternatively, if the patient is still available, flow may return to step 160 and a new series of image frames 150 may be acquired.

Once the user is satisfied that the anatomic landmarks are correct, flow passes to step 170, where the signal processor 116 defines an initial template contour template 190 based on the landmarks.

Figure 5:
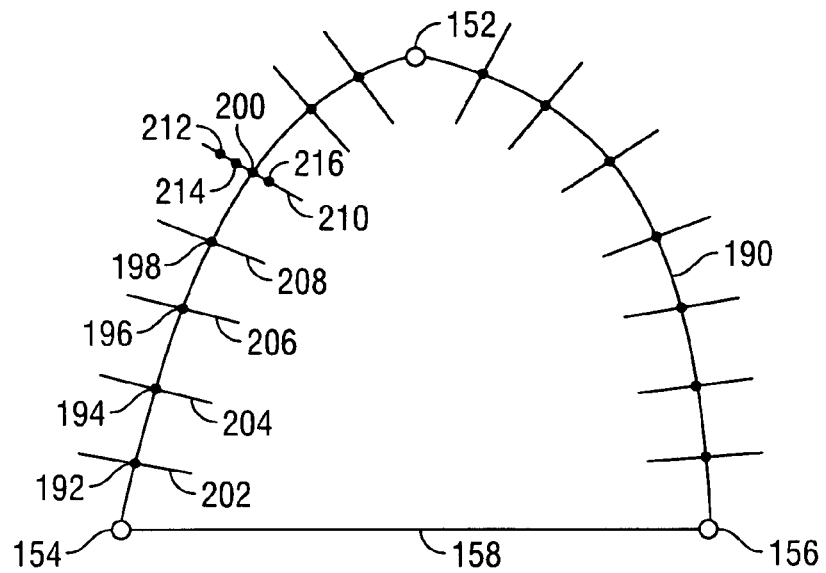
FIG. 5 illustrates a contour template with the apex and first and second ends of the AV plane identified in accordance with an embodiment of the present invention.

FIG. 5 illustrates a contour template, or contour template 190, with the apex 152 and first and second ends 154 and 156 of the AV plane 158 identified. The signal processor 116 defines the contour template 190 as a curved line that runs from the first end 154 of the AV plane to the apex 152, and from the apex 152 to the second end 156. The AV plane 158 is illustrated as a line joining the first and second ends 154 and 156. The contour template 190 and the line illustrating the AV plane 158 are not necessarily displayed on the display 118, but are used as an initial contour by the algorithm.

Returning to FIG. 4, a series of points 192-200 are defined along the contour template 190 in step 172. By way of example only, the number of points 192-200 may be 40 or less points. The locations of points 192-200 may be predefined by the signal processor 116, and may depend upon the anatomy or portion of anatomy being scanned. The signal processor 116 then defines paths 202-210 bisecting the contour template 190 at each point 192-200

In step 174, the signal processor 116 defines candidate points 212-216 along each path 202-210. Each path 202-210 may have 20 candidate points 212-216, although a larger or smaller number of candidate points may be used. The points 192-200, which previously defined the intersection of the contour template 190 and lateral paths 202-210, may also be used as candidate points. For clarity, not all of the points, paths, and candidate points along contour template 190 are identified and numbered in FIG. 5.

In step 176, each candidate point 212-216 along each path 202-210 is analyzed to determine a score (number or cost). The score may be based, in part, upon a predefined characteristic of the anatomic structure. For example, the intensity, or brightness, of all of the candidate points 212-216 along a path are compared with respect to each other. The intensity of the candidate points 212-216 are compared to locate the brightest and darkest areas of the path 210. In ultrasound, the tissue is typically brighter relative to the blood. Therefore, the best transition defining the endocardium along the path 210 may be identified as the largest difference in brightness going from dark to light between two or more neighboring candidate points 200 and 212-216. For example, 6, 8 or 10 neighboring points on a path 210 may be compared. Each candidate point 200 and 212-216 is given a score based upon the brightness comparison with respect to its neighbors. This score is used later in the method to locate endocardium.

Figure 6:
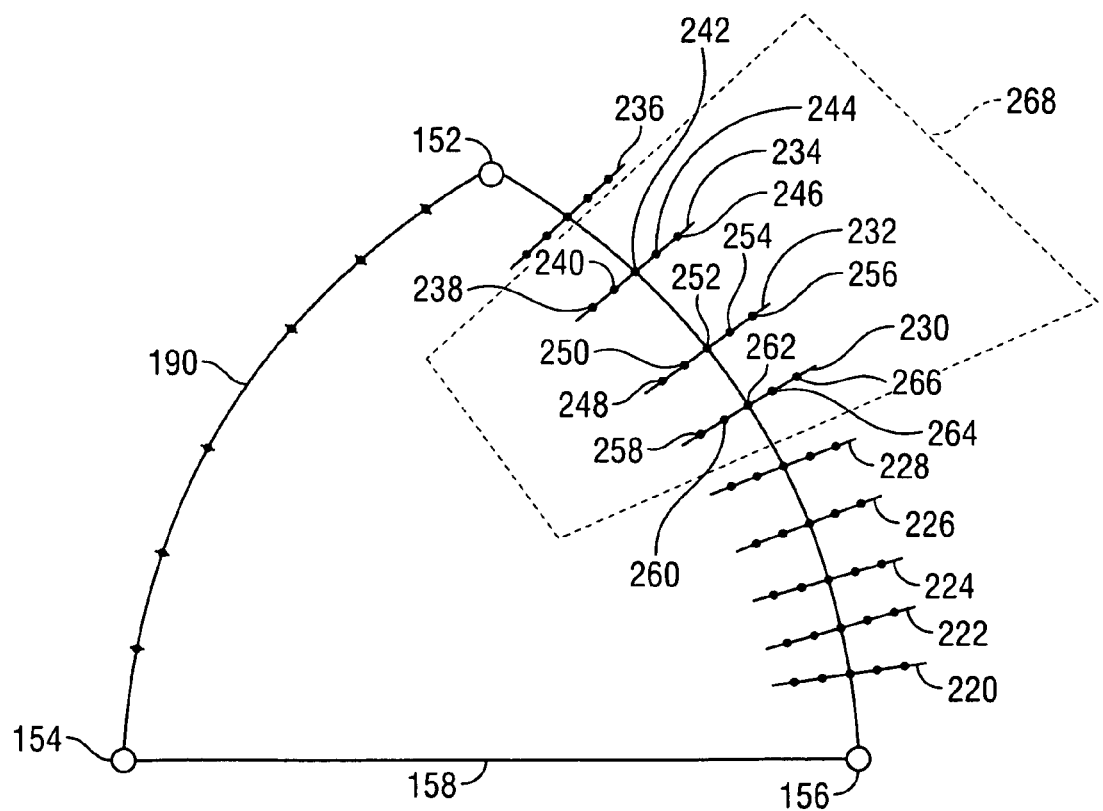
FIG. 6 illustrates the contour template and paths with candidate points formed in accordance with an embodiment of the present invention.

FIG. 6 illustrates the contour template 190 and paths 220-236 with candidate points 238-266. For clarity, not all of the candidate points on every path have been numbered.

In step 178 of FIG. 4, the signal processor 116 analyzes candidate points 238-266 between paths 220-236 to determine the best transition point on each path 220-236. The transition point defines the best location of the endocardium at this time during the method. The series of transition points will define a best path, being bright on the outside, indicating tissue, and dark on the inside, indicating blood.

A search region 268 may be defined around two or more consecutive paths 220-236. For example, candidate points 238-266 may be analyzed along the three consecutive paths 230-234. Each combination of three candidate points 238-266, one per path 230-234, is compared and assigned a cost based on the angle along the possible path, or the smoothness of the contour, between the three candidate points 238-266. The cost previously assigned in step 176 indicating being on the edge (transition from dark to bright) is also taken into consideration. Three sets of candidate points, for example [238, 248, 258], [238, 248, 260], [238, 248, 262], [238, 248, 264], and [238, 248, 266] are analyzed with respect to each other. Alternatively, two sets of candidate points, for example [238, 248], [238, 250], [238, 252], [238, 254] are analyzed relative to the contour template to estimate smoothness. The candidate points 238-266 on each path 220-236 having the best combination of being smooth and on the edge are assigned the most favorable cost, and thus are defined as transition points. For example, candidate points 244, 252, and 260 may be assigned to be transition points for paths 230-234, respectively, within search area region 268.

Therefore, the signal processor 116 scans along the contour template 190 to find a best path, scanning from the first end 154 to the apex 152, then to the second end 156. The search region 268 is moved along the contour template 190 from end 154 to the apex 152 and then to end 156 so that every combination of two or three candidate points 238-266 are analyzed along every two or three consecutive paths 220-236. The path that minimizes the cost of the analysis from step 176 and 178 is selected.

Figure 7:
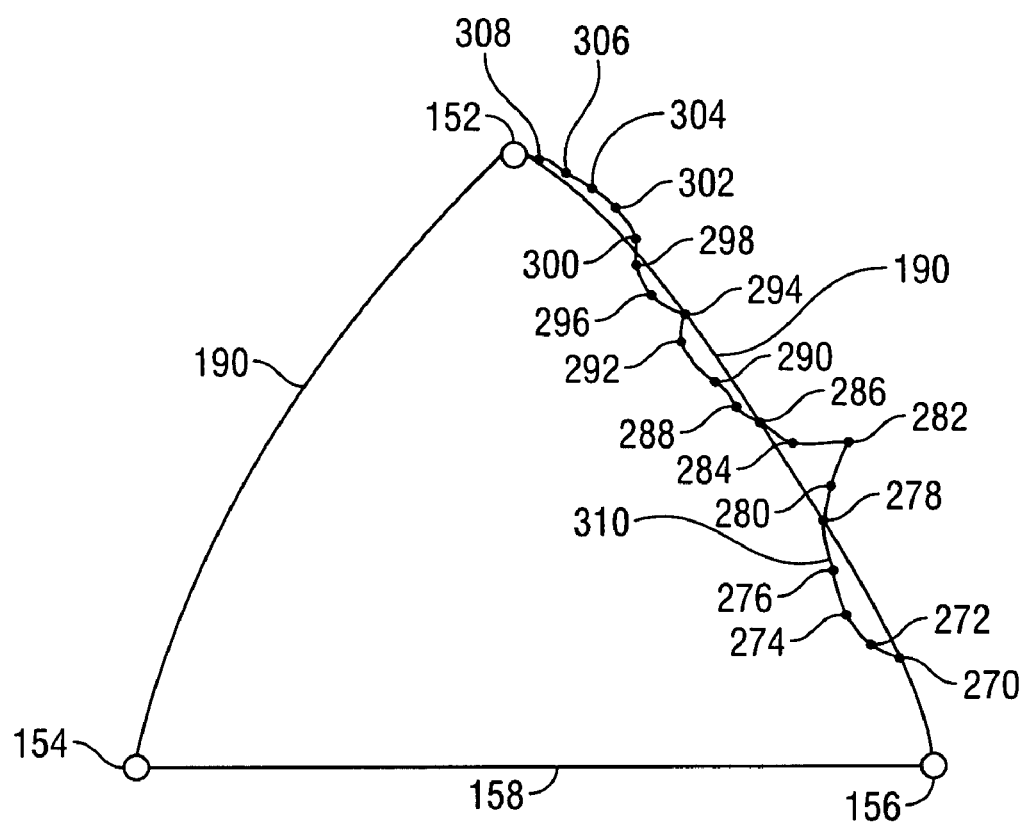
FIG. 7 illustrates the transition points which define a path in accordance with an embodiment of the present invention.

FIG. 7 illustrates the transition points 270-308 determined in step 178 of FIG. 4 which define a new contour, or path 310. The path 310 more closely follows the myocardium than the contour template which may previously have been drawn by the user or the ultrasound system 100.

Figure 8:
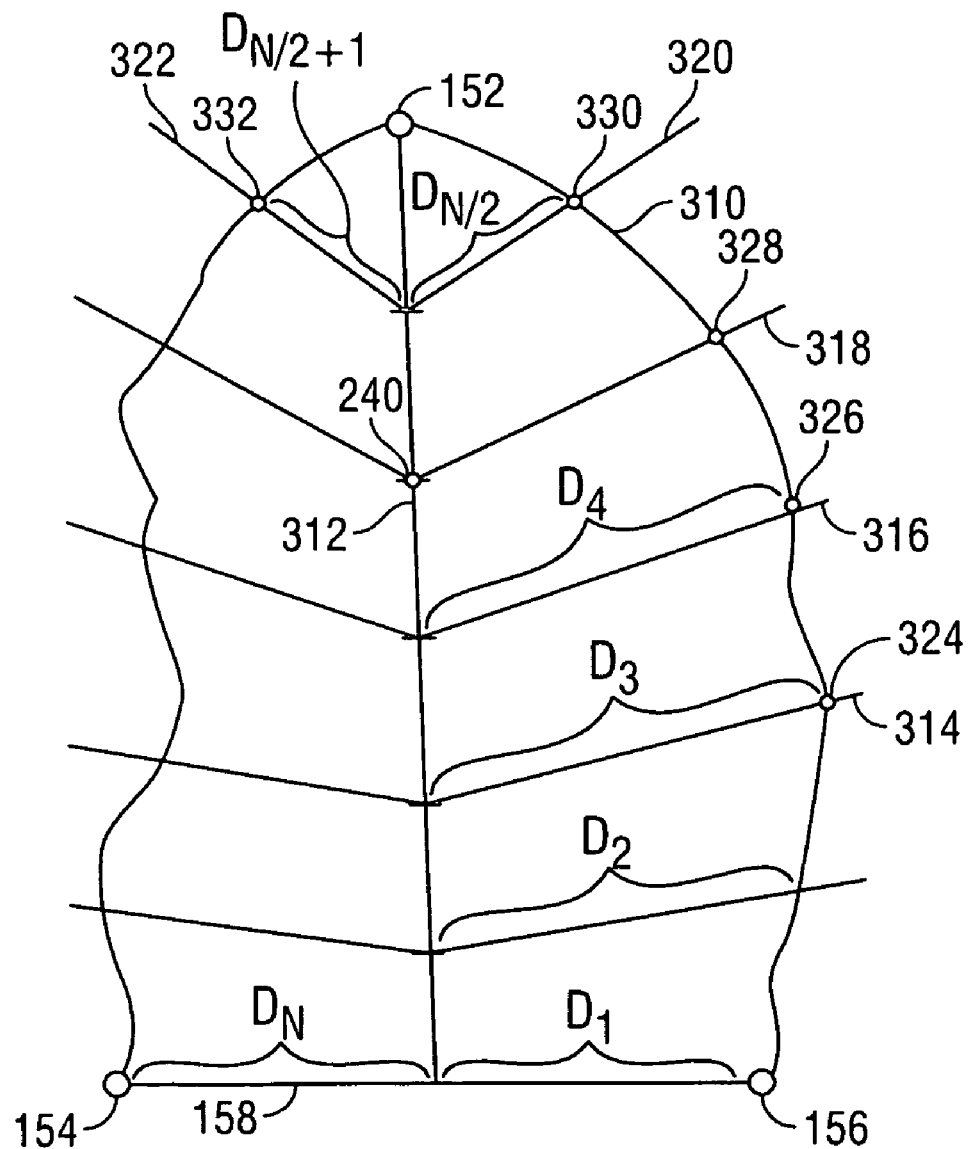
FIG. 8 illustrates an image frame with the path, which represents the endocardium as previously illustrated in FIG. 7, in accordance with an embodiment of the present invention.

Returning to FIG. 4, in step 180 the signal processor 116 spatially smoothes the path 310. FIG. 8 illustrates an image frame 150 with the path 310, which represents the endocardium as previously illustrated in FIG. 7. An LV major 312 is drawn from the apex 152 to the center point of the AV plane 158. Lines 314-322 are drawn from LV major 312 and outwards. It should be understood that more lines 314-322 may be used.

The signal processor 116 identifies an intersection point between each lines 314-322 and the path 310, or endocardium. For example, intersection point 330 is identified for the intersection between the line 320 and the path 310.

After the intersection points 324-332 have been identified, the signal processor 116 calculates the distance D from the intersection points 324-332 to the LV major 312 along each line 314-322. Therefore, for line 316, distance $D_4$ is calculated. The distances, such as $D_1$-$D_4$, are calculated for each line 314-322 and may be stored in a table format.

The distances $D_1$-$D_4$ are then smoothed in space to create a smoother appearance. The smoothing may be accomplished by calculating a running average or median of consecutive distances along the path 310. Alternatively, other linear or non-linear filters may be used. For example, three consecutive distances, such as distances $D_1$, $D_2$, and $D_3$, may be averaged together to create a smooth contour. The averaged consecutive distances are used to create a smoother path by possibly calculating a new position for intersection points 324, 326, 328, 330, and 332. By averaging the distances $D_1$-$D_4$, consecutive intersection points along the path 310 which are significantly different compared to their neighboring intersection points will be corrected (such as transition point 282 of FIG. 7). The resulting contour, or new path 310 may be saved in table, data set or vector format as a new set of distances $D_{1,4}$-$D_{4,4}$ for each image frame 150. The new set of distances $D_{1,4}$-$D_{4,4}$ represents the location of the myocardium for each image frame 150, such as in Table 1 of FIG. 9, discussed below.

Returning to FIG. 4, the signal processor 116 determines whether more frames 150 in the series of frames 150 are to be processed in step 182. If yes, flow returns to step 170 until each of the remaining image frames 150 is processed. The processor uses the contour identified for the previous image frame as one of the cost functions for the next consecutive image frame. If no image frames 150 remain to be processed, flow passes to step 184.

FIG. 9 and FIG. 10 illustrate two tables with distance measurements representing contours of image frames 150. The table shown in FIG. 9 comprises the distance measurements for the processed image frames 150 (after step 180), and the table shown in FIG. 10 comprises the averaged distance measurements after temporally smoothing the contours (after step 184). Image frame 1 is adjacent to image frame 2, image frame 2 is adjacent to image frame 3, and so on. To temporally smooth the contours in time, the signal processor 116 may use the median filter to filter the $D_{1A}$ values in Table 1 for image frames 1, 2 and 3, then store the filtered value in Table 2 for image frame 2. Alternatively, more than three consecutive contours may be filtered. In one embodiment, the signal processor 116 may use the value $D_{1AVE}$ in Table 2 for image frame 2, and filter it with the $D_{1A}$ values in Table 1 for image frames 3 and 4, and so on. Alternatively, instead of using a median filter, other non-linear or linear filters such as average filter may be used.

The distance values stored in Table 2 represent the final values for the contour of the endocardium for each image frame 150 within the heart cycle. When displaying the path 310 defined by the values in Table 2 in a cineloop, the path 310 will closely follow changes in the endocardium from image frame 150 to image frame 150, and the contour will appear smooth and not jumpy on the display system 118. When the contours for all the image frames 150 are located, the ventricle volume is estimated, e.g. by using Simpson's method. The image frame 150 with the smallest estimated ventricle volume during one heart cycle is defined as the end-systole frame. The image frame 150 with the largest estimated ventricle volume is defined as the end-diastole frame. Optionally, ECG information may be used to select the ED and ES frame. For example, the first frame after the ECG trig point may be defined as the ED frame. The user may use the user input 120 to manually choose a different image frame as the correct ED or ES contour, or move or redraw a contour or portion of a contour on one or more image frames 150, move the apex, move the AV plane, redraw portions of the contour, or change the timing. The apex can be moved while the cineloop is running because it is in the same location in every frame. When a new apex location is specified, the edge detection is rerun automatically. The AV plane is moving, so it cannot be corrected while the loop is running. Once satisfied with the apex detection, press a button to go to the ED frame. The user can use a rotary button or a push button to jump between the ED and ES frame, or scroll in time back and forth within cineloop to review the contours. The user may manually draw portions of the contour if the system was unable to find an appropriate transition, such as when shadowing is present. If a contour is manually corrected, the values in Table 2 are updated accordingly.

The values stored in Table 2 may now be used by the ultrasound system's measurement package. The area defined by the contour or path 310 represents the volume of the ventricle, and may be used to calculate ejection fraction, such as by using the Simpson's method. Stroke volume, CO, CI, MRE, E', A' and VS may also be calculated. In addition, if an average of multiple heart cycles is desired, previously calculated data may be saved to be combined with additional data.

Thus, as the path 310 more closely follows the endocardium compared to previous methods of drawing and automatic detection, calculations based upon the path 310 are more accurate. Persons skilled in the art will recognize the ability to apply the method and apparatus discussed to other imaging modalities, such as MRI, and anatomic structure other than the ventricle. In addition, other views of the heart may be evaluated, such as by using the long axis and aortic valve as landmarks. Also, trans-esophogial transducer may be used to view the heart, so the landmark detection will have to be adjusted.

While the invention has been described in terms of various specific embodiments, those skilled in the art will recognize that the invention can be practiced with modification within the spirit and scope of the claims.

What is claimed is:

1. A method for detecting an anatomic structure based on a medical diagnostic imaging data set, comprising:
   obtaining a data set representative of a diagnostic image corresponding to an anatomic structure using an imaging system;
   identifying at least one anatomic landmark within said data set;
   overlaying said data set with a contour template; and
   analyzing, using a processor, a search region of said data set surrounding said contour template to identify transition points associated with a predefined characteristic of the anatomic structure based at least on a transition smoothness.

2. The method of claim 1, further comprising defining contours for a series of images based on said contour template and said transition points and comparing said contours for adjacent images.

3. The method of claim 1, wherein said predefined characteristic of the anatomic structure is an interior edge of a chamber of the heart.

4. The method of claim 1, wherein said predefined characteristic of the anatomic structure is a wall of a chamber of the heart.

5. The method of claim 1, further comprising defining a series of paths traversing said contour template, along which said analyzing is performed.

6. The method of claim 1, further comprising defining a series of paths orthogonal to said contour template and searching for candidate transition points along said paths.

7. The method of claim 1, further comprising scoring candidate transition points within said search region based on at least one of a change in brightness, a smooth spatial transition between adjacent transition points in a diagnostic image, and a smooth temporal transition between corresponding transition points in other diagnostic images.

8. The method of claim 1, further comprising selecting a path through candidate transition points in said search region based on transition smoothness.

9. The method of claim 1, wherein said contour template estimates an outline of anatomic structure.

10. The method of claim 1, wherein said obtaining includes performing at least one of an ultrasound, CT, PET, SPECT, Gamma Camera, X-ray, and MR scan of an anatomy of interest.

11. The method of claim 1, wherein said obtaining includes loading a previously acquired data set.

12. The method of claim 1, wherein said anatomic structure constitutes the endocardium and said anatomic landmark constitutes at least one of a ventricle apex, a plane separating an atrium and ventricle, and a cardiac valve.

13. A system for identifying an endocardium, comprising:
   a transmitter for transmitting ultrasound signals into an area of interest;
   a receiver for receiving echo signals from transmitted ultrasound signals;

a memory for storing a series of image frames comprising said echo signals, said series of image frames comprising at least one heart cycle;

a signal processor processing said series of image frames to identify at least one of an apex and an AV plane having first and second ends, said signal processor overlaying a contour template connecting said apex to said first and second ends on said series of image frames, said signal processor identifying and comparing points along said contour template to identify transition points based upon a predefined characteristic of an endocardium and a transition smoothness; and an output for outputting information based on an output of said signal processor.

14. The system of claim 13, further comprising said signal processor defining paths transverse to said contour template, said paths intersecting said points, said signal processor defining at least two candidate points along each said path and comparing said at least two candidate points to each other with respect to said predefined characteristic.

15. The system of claim 13, further comprising a user input for adjusting at least one of said apex and said first and second ends of said AV plane.

16. The system of claim 13, further comprising said signal processor comparing said transition points in adjacent image frames within said series of image frames, said signal processor moving at least one said transition point in a first adjacent image frame based upon at least one transition point in at least one adjacent image frame.

17. A method for identifying at least one of a contour between different types of tissue and a contour between tissue and blood, said method comprising:
obtaining a series of data sets representative of a diagnostic image having at least two different types of tissue using an imaging system;
identifying at least two anatomic landmarks within said series of data sets;
connecting said at least two anatomic landmarks with a contour template;
identifying data points on and around said contour template; and
comparing, using a processor, said data points to identify transition points having a predefined characteristic indicative of a change from one type of tissue to one of a second type of tissue and blood based at least on a transition smoothness.

18. The method of claim 17, further comprising:
identifying multiple corresponding transition points on adjacent data sets within said series of data sets; and
adjusting a location of a corresponding transition point based upon an average of said multiple corresponding transition points.

19. The method of claim 17, further comprising:
said identifying data points further comprising defining paths being transverse with respect to said contour template, said data points being identified along said paths;
said comparing further comprising comparing said data points located along multiple said paths; and
adjusting a location of at least one said transition point based upon an output of said comparing.

20. The method of claim 17, further comprising:
said identifying data points further comprising defining paths being transverse with respect to said contour template, said data points being identified along said paths;
said comparing further comprising comparing said data points located along the same said path; and
assigning a score to each said data point based on an output of said comparing.

21. The method of claim 17, further comprising:
said identifying data points further comprising defining paths being transverse with respect to said contour template, said data points being identified along said paths;
said comparing further comprising comparing said data points located along a first set of adjacent paths;
adjusting a location of at least one said transition point based upon an output of said comparing; and
said comparing further comprising comparing said data points located along a second set of adjacent paths, said first and second sets comprising at least one common path, said data points including at least one said transition point previously adjusted.

* * * * *